(12) United States Patent
Biazik et al.

(10) Patent No.: US 7,149,342 B2
(45) Date of Patent: Dec. 12, 2006

(54) DEVICE AND METHOD FOR INVESTIGATING PREDETERMINED AREAS OF PRINTED CIRCUIT BOARDS

(75) Inventors: Andrzeij Biazik, Tomaszow Mazowiecki (PL); Mariusz Piecek, Warsaw (PL); Viktor Romanov, Wertheim (DE)

(73) Assignee: atg test systems GmbH & Co. KG, Wertheim (DE)

( * ) Notice: Subject to any disclaimer, the term of this patent is extended or adjusted under 35 U.S.C. 154(b) by 775 days.

(21) Appl. No.: 10/298,342

(22) Filed: Nov. 18, 2002

(65) Prior Publication Data
US 2003/0059102 A1   Mar. 27, 2003

Related U.S. Application Data

(63) Continuation of application No. PCT/EP01/04518, filed on Apr. 20, 2001.

(30) Foreign Application Priority Data
May 24, 2000  (DE) ................ 100 25 751

(51) Int. Cl.
*G06K 9/00* (2006.01)
(52) U.S. Cl. ..................... 382/148
(58) Field of Classification Search ......... 382/141–152
See application file for complete search history.

(56) References Cited

U.S. PATENT DOCUMENTS

| | | | | |
|---|---|---|---|---|
| 4,469,553 A | | 9/1984 | Whitehead | 156/627 |
| 4,549,206 A | * | 10/1985 | Suzuki et al. | 348/126 |
| 4,747,146 A | * | 5/1988 | Nishikawa et al. | 382/112 |
| 4,764,969 A | * | 8/1988 | Ohtombe et al. | 382/148 |
| 5,048,094 A | | 9/1991 | Aoyama et al. | 382/8 |
| 5,134,575 A | * | 7/1992 | Takagi | 382/147 |
| 5,204,912 A | * | 4/1993 | Schimanski | 382/147 |
| 5,369,431 A | | 11/1994 | Levy et al. | 348/126 |
| 5,513,099 A | | 4/1996 | Schein | 364/167.01 |
| 5,903,160 A | | 5/1999 | Ianenko et al. | 324/537 |
| 5,977,776 A | | 11/1999 | Huth et al. | 324/537 |
| 6,340,893 B1 | | 1/2002 | Prokopp | 324/754 |

(Continued)

FOREIGN PATENT DOCUMENTS

DE       37 37 869       5/1989

(Continued)

OTHER PUBLICATIONS

PCT/US94/12703, May 1995, Wasserman.*

(Continued)

*Primary Examiner*—Joseph Mancuso
*Assistant Examiner*—Hadi Akhavannik
(74) *Attorney, Agent, or Firm*—Houston Eliseeva LLP (57) ABSTRACT

A method for examining a circuit board in a predetermined area of the circuit board uses an apparatus that has a stationary camera and a display unit. The circuit board is arranged so as to be freely movable in the scanning zone of the camera. According to the invention, an image of the circuit board recorded by the camera, the camera image, is brought into congruence with a circuit board image, wherein the camera image and the circuit board image, after a first alignment process, are enlarged at least once in the same ratio and then re-aligned. This results in even greater congruence between camera image and circuit board image, and the predetermined area to be examined is marked in this enlarged view. In this way a user of the method according to the invention may rapidly locate the area of the circuit board to be examined, in an enlarged display, and may analyze it accordingly.

36 Claims, 11 Drawing Sheets

U.S. PATENT DOCUMENTS 6,434,264 B1 * 8/2002 Asar .......................... 382/147
6,937,754 B1 * 8/2005 Eguchi ....................... 382/145

FOREIGN PATENT DOCUMENTS

| DE | 40 27 902 | 3/1992 |
| DE | 197 09 939 A1 | 9/1998 |
| EP | 0 386 924 A2 | 9/1990 |
| EP | 0 468 153 A1 | 1/1992 |
| EP | 0 578 816 B1 | 1/1994 |
| EP | 0 632 689 B1 | 6/1994 |
| WO | WO 95/12952 | 11/1994 |
| WO | WO 01/91053 A1 | 11/2001 |

OTHER PUBLICATIONS

Kurt Michel: Die Mikrophotographie, 3. Auflage, Wien u.A.: Springer 1967, Seiten 501-502 (Abstract only).

* cited by examiner

DEVICE AND METHOD FOR INVESTIGATING PREDETERMINED AREAS OF PRINTED CIRCUIT BOARDS

This is a continuation of International Application PCT/EP01/04518, filed on Apr. 20, 2001, which was published in German under PCT Article 21(2), and which claimed priority to German application No. DE 100 25 751.8 (May 24, 2000), the contents of both applications being incorporated herein by this reference.

BACKGROUND OF THE INVENTION

U.S. Pat. No. 4,469,553 discloses an apparatus for the assembly, testing, and repair of circuit boards. This apparatus has a work surface for accommodating and retaining a circuit board, which is to be assembled. The circuit board is fixed to this holding surface by means of suction elements. A half-silvered mirror is positioned just above the work surface, and above the half-silvered mirror is an image projector. The image projector is used to project images of the components to be inserted and the track data on to the mirror. A user of the apparatus, looking through the half-silvered mirror, sees the image projected on to the half-silvered mirror by the projection equipment, together with the circuit board positioned behind. The user thus has the impression that this projected image is projected onto the circuit board, thereby marking the locations to be equipped with a relevant circuit component.

U.S. Pat. No. 5,513,099 describes an apparatus for the repair and processing of circuit boards. This apparatus has a work surface on which a circuit board to be examined may be fixed. A camera is mounted above the work surface, on a slide mechanism, which may be moved in a horizontal plane. The camera is capable of being located automatically over any desired point of the circuit board, which is to be examined. This apparatus has a computer with a video screen, a keyboard and a computer mouse.

Using this apparatus, a circuit board to be examined is fixed on the work surface. A digital image of the circuit board is then generated by the camera and displayed on the screen. The so-called "GERBER" data are superimposed on this image. The operator may then enter defect information, causing the camera to be positioned automatically over the section of the circuit board to which the defect information relates. The operator may then enlarge the camera image together with the image of the "GERBER" data. In this way the operator may observe and analyze the relevant area using an enlarged view.

SUMMARY OF THE INVENTION

The invention is directed to the problem of defining a method for examining a circuit board, and specifically a predetermined area of the circuit board, and an apparatus for implementing the method, in which an enlarged image of the predetermined area must be quickly and easily found and observed. It is desirable that the apparatus used to implement the method be very simple and cost-effective.

In general, according to one aspect, the invention features a method of examining a circuit board, and preferably a predetermined area of the circuit board. It uses an apparatus that has a stationary camera and a display unit. The method comprises a number of steps. Specifically, the circuit board is positioned for examination in the scanning zone or field of the camera. A camera image and a circuit board image, separate from the camera image, are shown on the display unit at the same scale. The circuit board to be examined is moved to make the camera image as congruent as possible with the circuit board image. An enlargement of the camera image and the circuit board image are made on the display unit in the same ratio. The camera image is brought to coincide more closely with the circuit board image. And, the predetermined area to be examined is displayed so that an enlarged view of the predetermined area of the circuit board to be examined is visible on the display unit.

In order to implement the method according to the invention, it is sufficient to have a stationary camera linked to a display unit, which may for example be the video screen of a conventional computer. The circuit board to be examined is placed in the scanning zone of the camera, in which it is freely movable. The display unit will show a camera image, i.e. the image of the circuit board captured by the camera, and a circuit board image, which is independent of the camera image and shows essential features of the circuit board. Both the camera image and the circuit board image are shown on the same scale. By moving the circuit board to be examined, the camera image is made to coincide with the circuit board image as closely as possible. The camera image and the circuit board image are then enlarged in the same ratio or to the same degree. By moving the circuit board again, the camera image is brought even more precisely into congruence with the circuit board image.

With this alignment of the camera image relative to the circuit board image, in at least two stages, it is possible to obtain a very precise overlay of the two images, without the need for any other major technical requirements in terms of mechanical precision, for example.

Thus, in the method according to the invention, a rough alignment is made first. As soon as this rough alignment is completed, a fine alignment is made. This involves enlargement of the overlapping images so that the deviations between the circuit board image and the camera image, which were not detectable at the scale used in the rough alignment, become discernible. Accordingly, by means of this step-by-step enlargement and just by moving it over a smooth surface, the circuit board may be aligned very precisely with reference to a greatly enlarged image.

Since in the case of a greatly enlarged image of the circuit board on the video screen in which only a part of it is visible, it is in practice impossible to align a circuit board with reference to such a part, unless the circuit board has been aligned at least roughly beforehand. The step-by-step enlargement according to the invention, of a circuit board to be examined with reference to a circuit board image, consequently allows for a rapid and precise alignment to a greatly enlarged circuit board image.

According to a preferred embodiment of the invention, one area of the display unit shows the circuit board image and the camera image, while another area shows a computer aided design (CAD) image. The CAD image shows the visible circuit board test points and tracks. The two areas are adjacent and the corresponding images (circuit board image, camera image, CAD image) are all shown on the same scale so that the camera image, which depicts the physical circuit board configuration, and the CAD image, may be compared on the display unit, and any deviations may be classed as defects.

According to a further preferred embodiment of the invention, two further areas of the display unit show respectively a defect list and a complete circuit board image, in which the area of the circuit board to be examined as currently being captured by the camera is plotted.

A circuit board to be examined is preferably tested in a circuit board tester. On the basis of the measurements made there, a defect file is generated. The defect file contains a list of all potential defects determined by the measurements. This circuit board is then examined by the method according to the invention, wherein the defect location determined by the circuit board tester represents a predetermined area of the circuit board for examination. All these areas are examined in succession, by first aligning the circuit board roughly relative to a circuit board image, and then aligning it more precisely in an enlarged view of the camera image and the circuit board image. The predetermined area to be examined is shown on the display unit so that the operator can see which area is to be analyzed. Here the individual steps are preferably activated by a single key, e.g. in the form of a control pedal.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

Using the embodiment, described in detail hereinbelow, of the method for examining a circuit board 1 (FIG. 3) according to the principles of the present invention, circuit board defects that have been found or isolated by using a circuit board tester 2 (see FIGS. 1 and 2) should be made visible or apparent to a user quickly and easily in an enlarged view. This is achieved by the use of a checking apparatus 3, shown in FIGS. 1 and 2. Thus, a defect that has been found via electronic analysis using circuit board tester 2 may then be viewed and further characterized using the inventive apparatus and method by enabling the user to observe the defect and surrounding portions of the circuit board 1.

Figure 1:
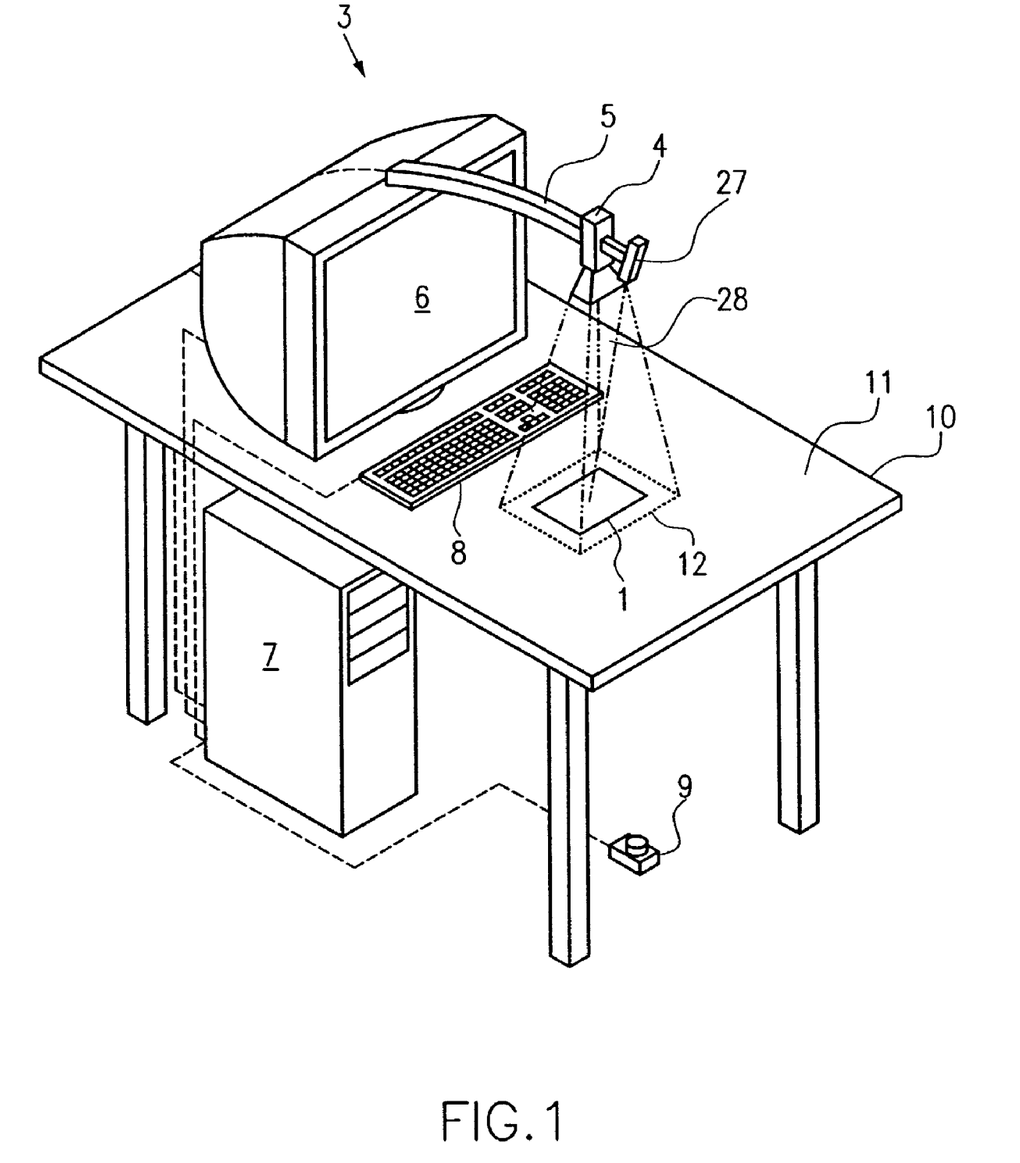
FIG. 1 is a perspective view of an apparatus according to the invention for examining a circuit board in a predetermined area of the circuit board.
Figure 2:
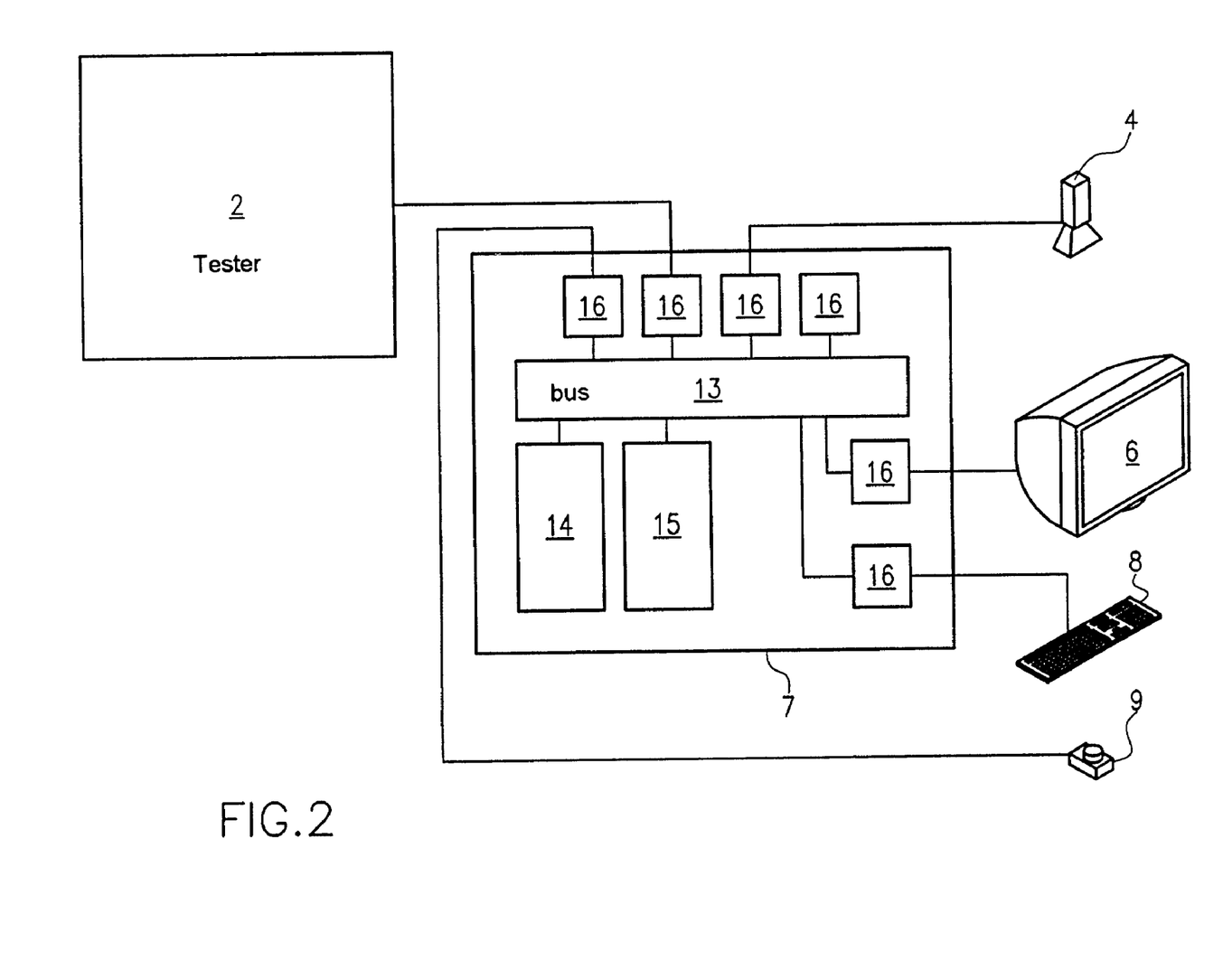
FIG. 2 is a block diagram of the apparatus of FIG. 1.

In more detail, with reference to FIGS. 1 and 2, the circuit board tester 2 is a parallel tester, as disclosed, for example, in EP 0 875 767 A2 (see U.S. Pat. No. 6,340,893), or a finger tester as described in EP 0 468 153 A1 and EP 0 853 242 A1 (see U.S. Pat. No. 5,977,776) respectively, in one implementation.

The checking apparatus 3 has a stationary camera 4, which, in the present embodiment, is fastened by means of a retaining bar 5 to the upper edge area of a video screen 6. A light pointer 27, emitting a focused light beam 28, may optionally be fastened to the retaining bar 5 alongside the camera 4. The camera 4 and the video screen 6 are electrically linked to a computer 7. Also connected to the computer 7 are a keyboard 8 and a control pedal 9. The video screen 6 is mounted with the camera 4 on a table 10. The tabletop 11 forms the work surface on which the circuit board 1 to be examined is placed. The camera 4 is mounted just above the tabletop 11, with its scanning zone 12 directed on to the tabletop 11.

The computer 7 is a conventional personal computer with a data bus 13 to which a CPU 14 and a data memory 15 are connected. Also connected to the data bus 13 are interface cards or facilities 16, providing interfaces to the keyboard 8, the video screen 6, the camera 4, and the control pedal 9. The computer 7 is also connected via an interface facility 16 to the circuit board tester 2.

The camera 4 is a CCD camera with a resolution of 752×582 pixels, in a one implementation. It has an electronically-controllable zoom lens with a focal range from 4.1 mm to 73.8 mm. A SONY camera, model FCB-IX47P, may for example, be used. Such cameras are standard products that can be obtained easily and at an economical price.

The light pointer 27 is preferably in the form of a laser.

Figure 3:
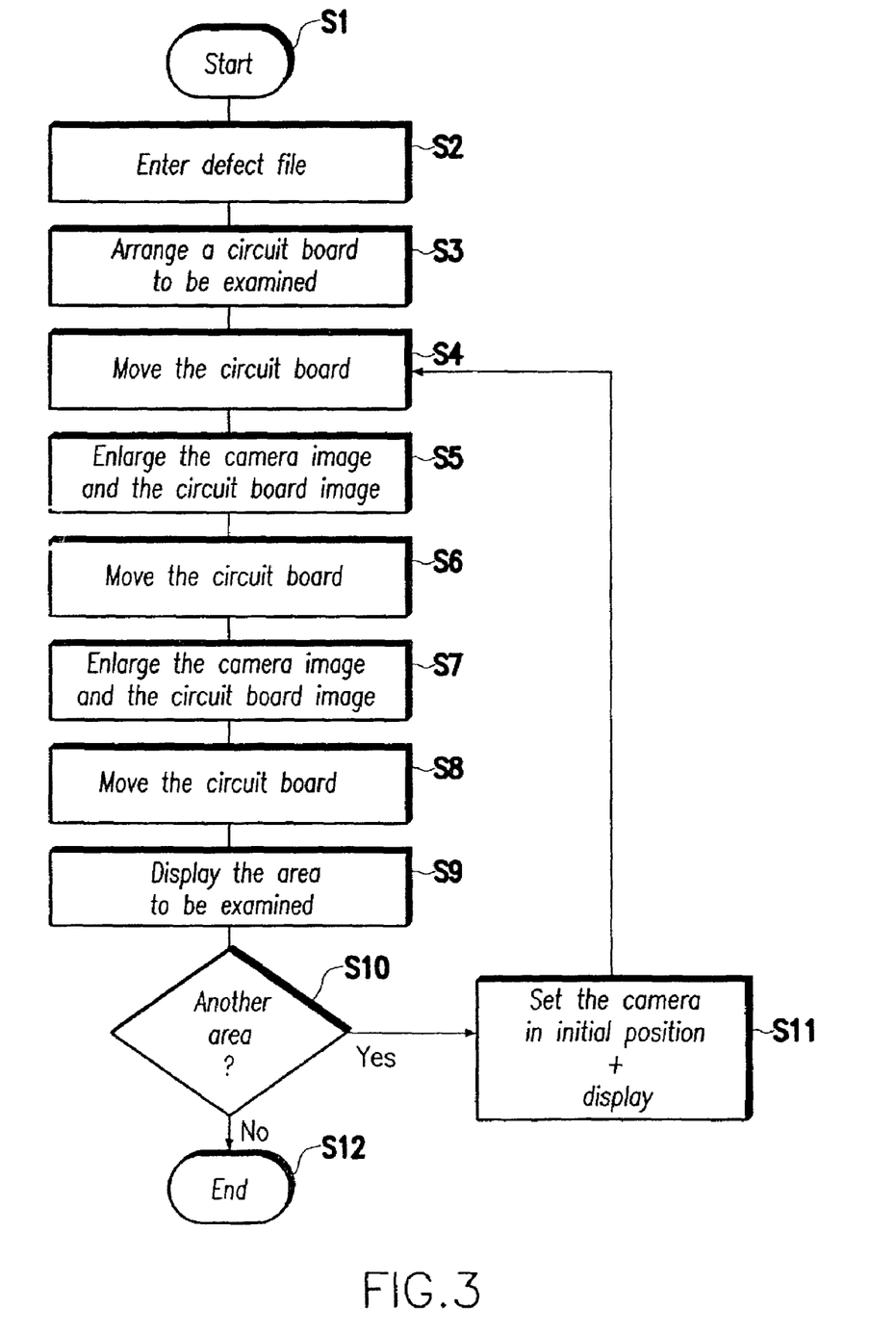
FIG. 3 is a flow chart showing a method according to the invention.

FIG. 3 shows the method, according to the invention, of examining a circuit board in a predetermined area of the circuit board. The explanation is made with reference to the screen displays shown in FIGS. 4a to 4g.

The method according to the invention is preferably realized as a computer program, which is stored in the data memory 15 of the computer 7. After the computer has been switched on and the program initialized, the program and the method according to the invention respectively are started by actuating the control pedal 9 (step S1). This brings the zoom lens of the camera 4 into an initial position (focal length of=4.1 mm), so that the scanning zone 12 of the camera 4 covers an area on the tabletop 11 measuring, for example, 400 mm×300 mm or larger. Such a scanning zone is greater than the majority of circuit boards to be examined. With larger circuit boards, only part of them will be covered, however.

On the video screen 6, four independent displays are shown, each in a section or window 17 to 20 (FIGS. 4a to 4g). Window 17, displayed at the top left of the video screen 6, shows an image 26 of the circuit board 1 to be examined, which is generated from CAD data and includes both circuit board test points and individual tracks or conductive traces. This CAD image 26 is based on the circuit board test point data and track data used for the measurements in the circuit board tester 2, and shows the circuit board to be tested in a basically defect-free form.

Shown in window 18, displayed at top right of the video screen, is a circuit board image 24 containing some of the circuit board test points of the circuit board to be examined. This circuit board image 24 contains information on the circuit board to the extent necessary to align a camera image—explained in detail below—of a circuit board 1 to be examined, relative to the circuit board image. It is therefore expedient not to show all circuit board test points and tracks in the circuit board image 24, since this multiplicity of information is not needed to align the camera and would tend to be distracting.

In step S2, a defect file is transmitted from the circuit board tester 2 to the checking apparatus 3, and the defects are displayed in a list in window 19.

The list of defects, which was determined in advance by the circuit board tester 2, is displayed in window 19 at the bottom left of the video screen 6. This list is displayed in the form of a table and has several columns, indicating the number of the defect (No), the measuring run (Run), the number of the circuit board (Panel), the fault type (Fault type), the first circuit board test point (Pad1) and the second circuit board test point (Pad2), and the measured value (Measured value). In the case of the defect types, a distinction is generally made between breaks (open) and short circuits (short). Measurements are usually two-point measurements between two circuit board test points, in which the resistance of the track or trace running between them is measured. The relevant resistance value is shown as the measured value in the table.

If the circuit board tester 2 uses a different method of measurement, in which, for example, only one circuit board test point is contacted, then the table should be modified accordingly. Such a method is known for example from U.S. Pat. No. 5,903,160.

At the start of the program, the CAD image 26 and the circuit board image 24 respectively are shown in windows 17 and 18 in such a way that the area of the circuit board 1 to be examined is roughly in the center of each window 17, 18. In the present embodiment, the area to be examined is preset by a circuit board test point connected to a track, which has been judged to be defective on the basis of the preceding measurement.

These circuit board test points are each marked by a horizontal arrow 21 and a vertical arrow 22. In the embodiment shown in FIGS. 4a to 4g, both circuit board test points connected to the track judged to be defective are marked by suitable arrows 21, 22, while circuit board images 24 and CAD images 26 are shown in FIGS. 4a to 4f aligned centrally with reference to the upper circuit board test point in the respective window 17, 18, and in FIG. 4g aligned centrally with reference to the lower circuit board test point.

In window 19, the current defect to be examined is emphasized in the table by inversion or highlighting of the relevant line.

In window 20, the whole of the circuit board 1 to be examined is shown in the display of the circuit board image of window 18, with the area of the circuit board to be examined as displayed in windows 17 and 18 marked by a frame 23. Also marked are crosshairs 29, the intersection point of which marks the circuit board test point to be examined.

Figure 4A:
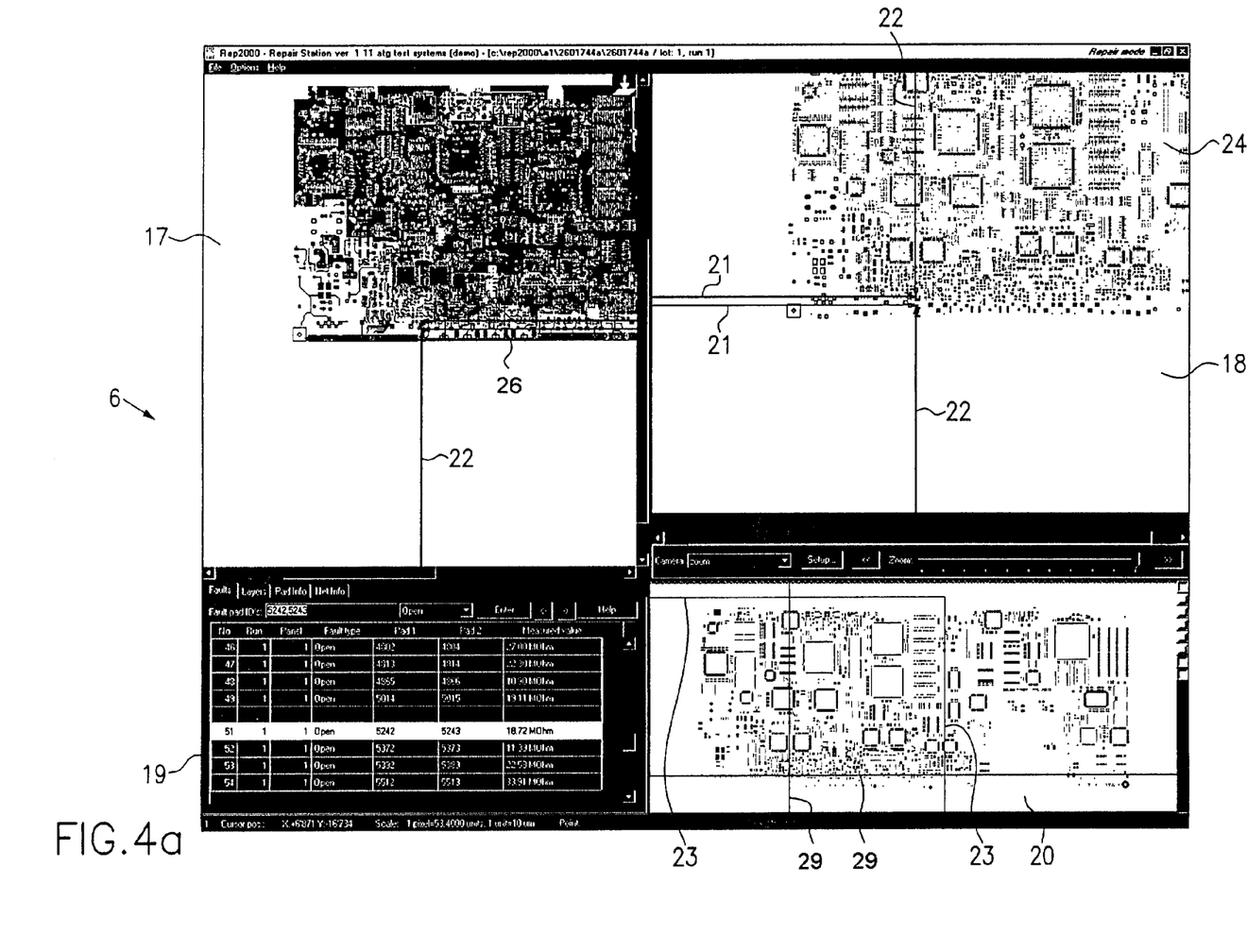
FIGS. 4a to 4g are screen displays for the individual steps of the method according to the invention as set out in FIG. 3.
Figure 4B:
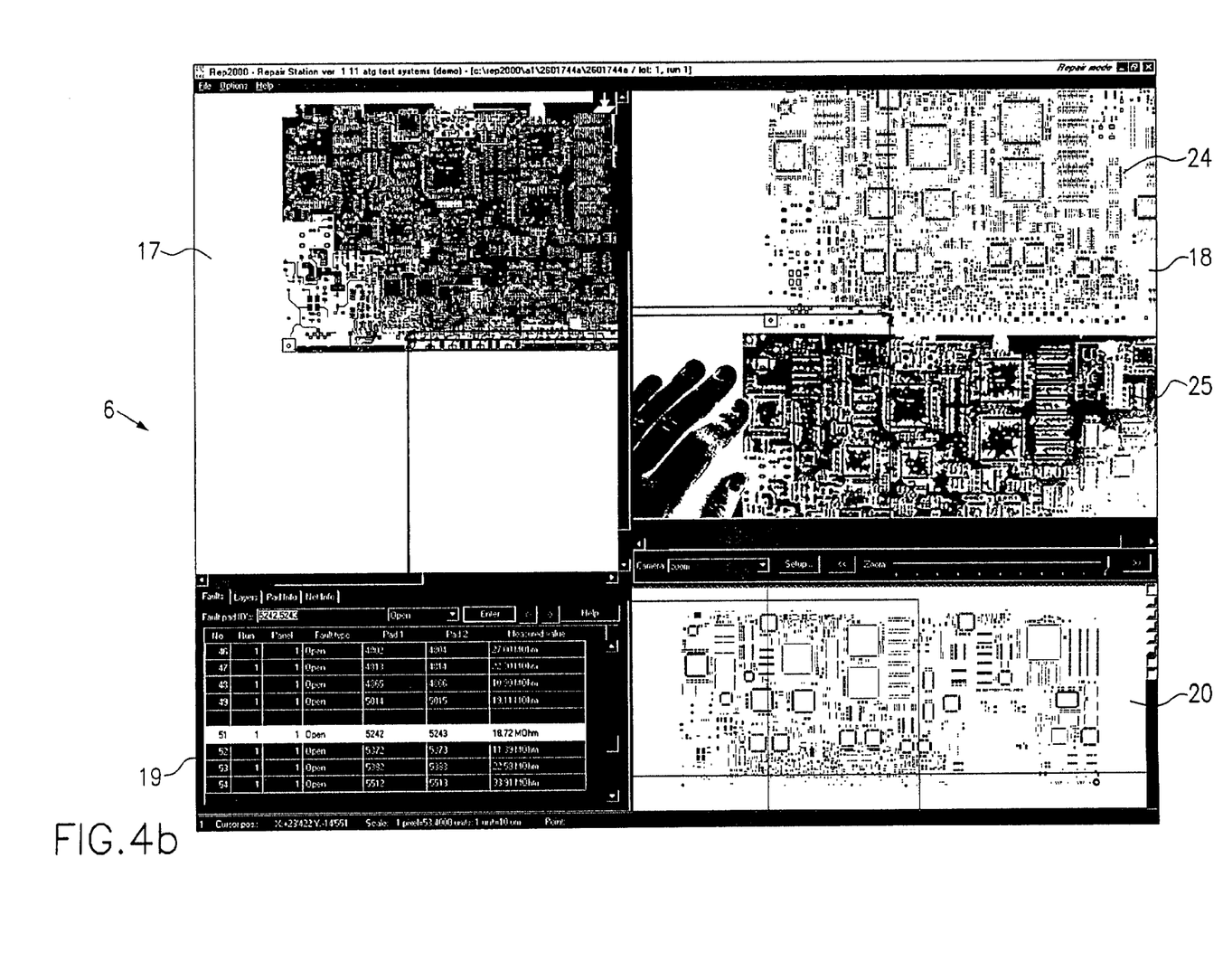

In step S3 the circuit board 1 to be examined is arranged on the tabletop 11 in the scanning zone 12 of the camera 4 (FIG. 4b). The camera 4 scans the circuit board and generates a digital camera image 25 of the circuit board to be examined. This camera image 25 is displayed in window 18.

Figure 4C:
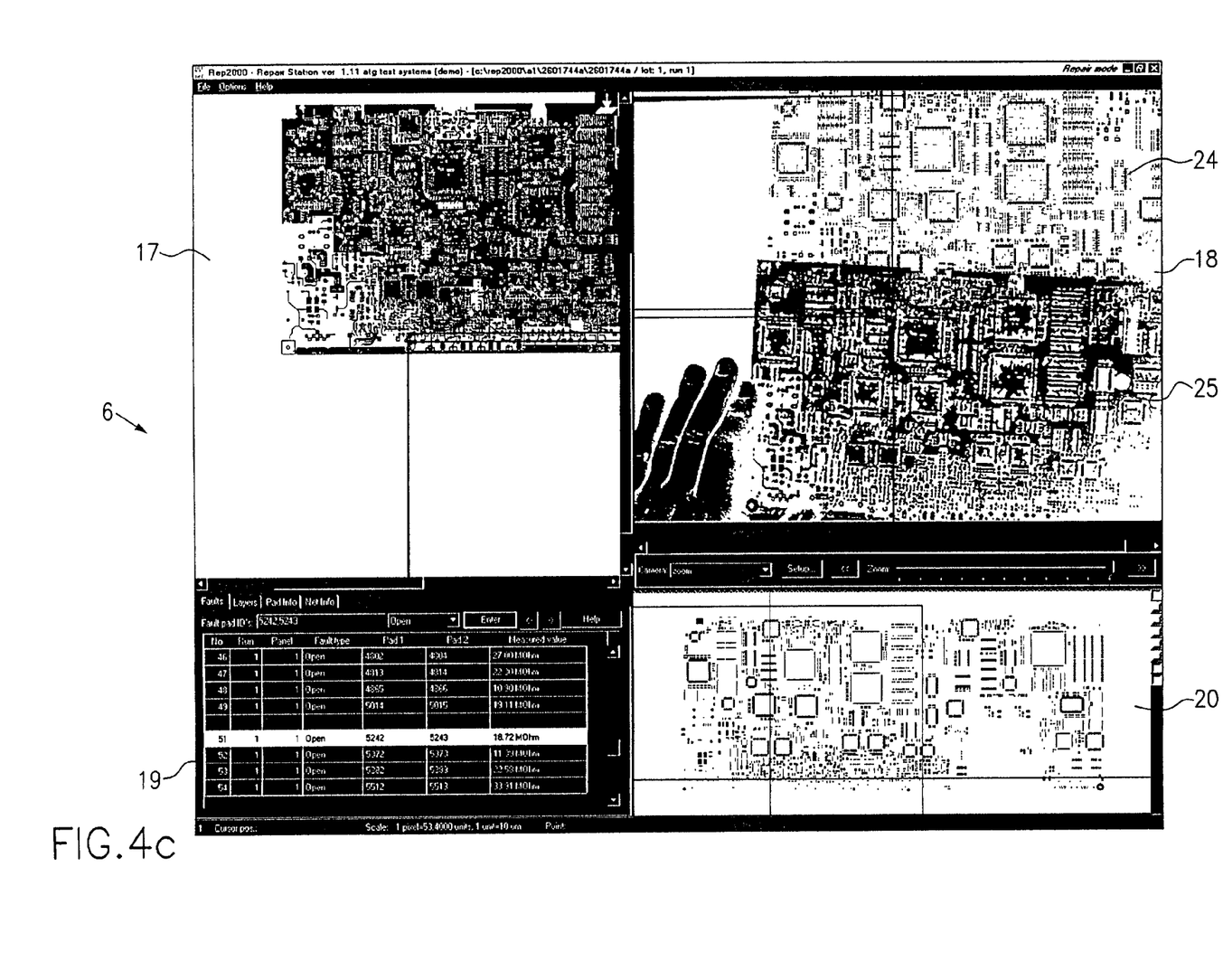
Figure 4D:
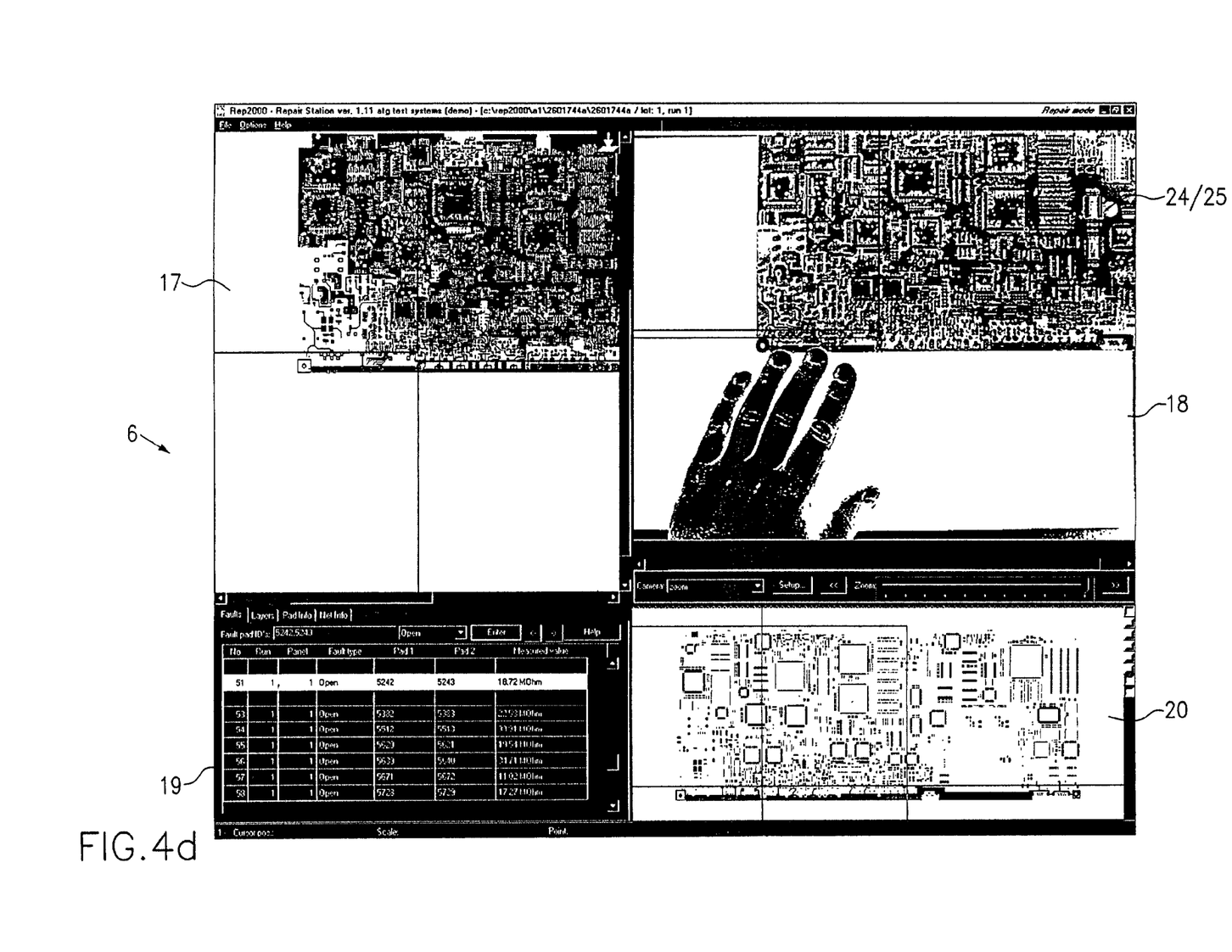

The circuit board is now shifted until the camera image 25 and the circuit board image 24 coincide in window 18 (step S4). This brings the circuit board 1 into alignment with the circuit board image 24. This process is illustrated in FIGS. 4b–4d.

Figure 4E:
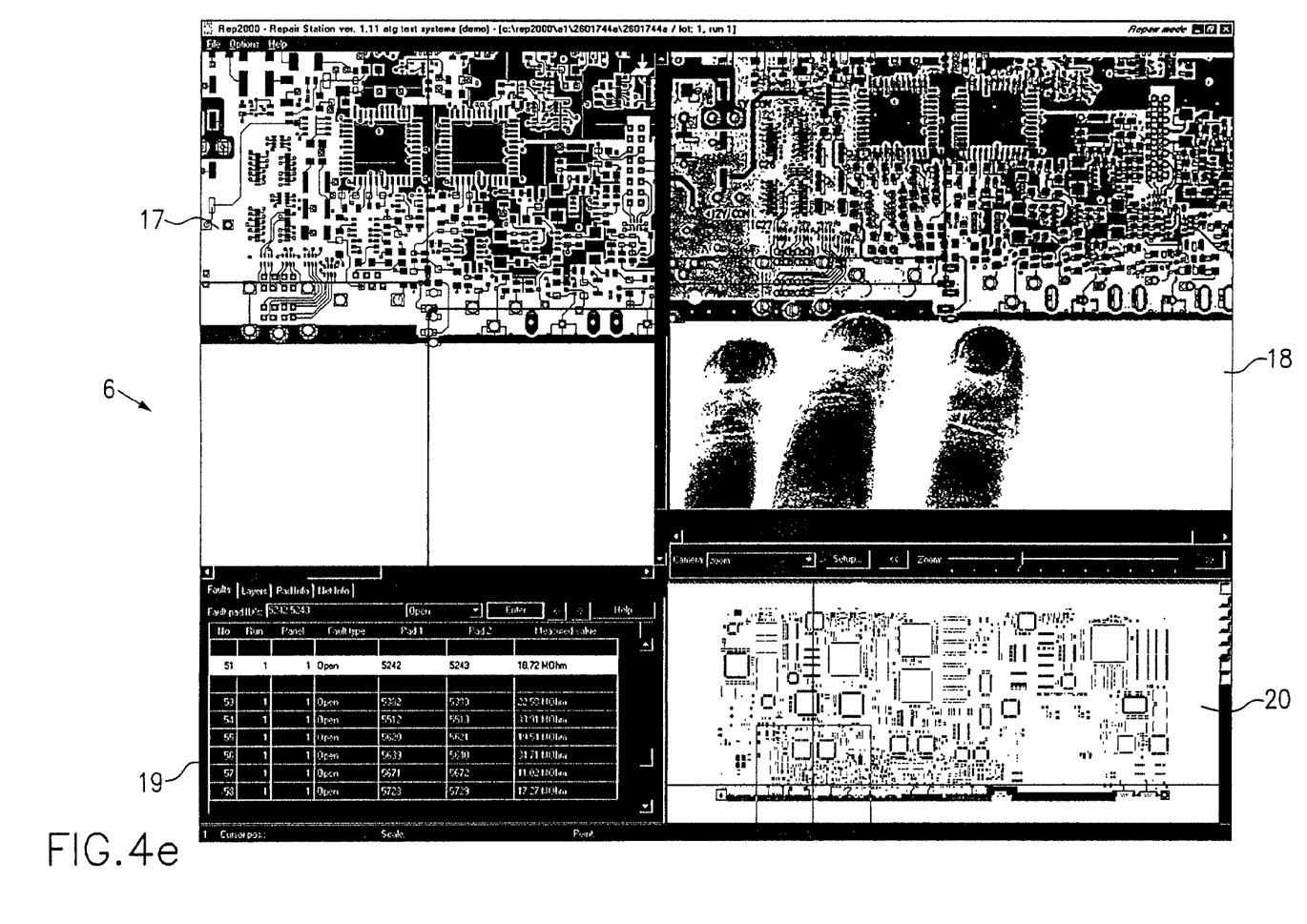

By again operating the control pedal 9, the camera image 25 and the circuit board image 24 are enlarged in the same ratio (step S5). The enlarged display enables the operator of the checking apparatus to see clearly the differences between the camera image 25 and the circuit board image 24. The circuit board 1 is then shifted again (step S6) to bring the camera image 25 more precisely into line with the circuit board image (FIG. 4e).

In step S7 the camera image 25 and the circuit board image 24 are again enlarged by the same ratio, and the circuit board 1 is again shifted in step S8 to obtain even more precise congruence between the camera image 25 and the circuit board image 24.

In principle it would also be possible to make the two enlargements of the camera image and the circuit board image of steps S5 and S7 in a single stage. But, in practice it has been found that an enlargement by a factor of more than 20 is not effective, since the differences after the first alignment in step S4 between the camera image 25 and the circuit board image 24 are still so great that with such an enlargement, in which only a small part of the circuit board is still visible, fresh alignment is often difficult, especially if the circuit board has a very even and regular grid of circuit board test points in the area displayed.

Once the circuit board image 24 and the camera image 25 are displayed in window 18 in the maximum desired enlargement, the area to be examined must be marked (step S9). This marking is effected by means of the horizontal arrow 21 and the vertical arrow 22, which point to the circuit board test point. In the present embodiment these arrows are shown right from the start of the procedure (step S1). In the context of the invention, it is of course also possible to show these arrows or other suitable markings only after the maximum desired enlargement has been made.

The light pointer 27 is set so that its light beam 28 marks the point on the circuit board 1 corresponding to the area to be examined. Since this area is always in the center of the window 17, the point marked by the light beam is always at the same point on the work surface, represented in the present embodiment by the tabletop 11. It is therefore necessary to adjust the light pointer only once. It then remains stationary during implementation of the method according to the invention.

When the user of the method according to the invention has finished studying the circuit board test point and the associated track to be examined (FIG. 4f), then he operates the control pedal, thereby causing the program sequence to move forward to step S10. In this step, an inquiry is made as to whether the list displayed in window 19 contains a further circuit board test point to be examined. If the inquiry reveals that there is a further circuit board test point to be examined, then the program sequence moves on to step S11, in which the camera is once again set in the initial position (focal distance fo) and the circuit board image 24 is displayed in window 18 on the same scale as the further circuit board test point to be examined in the center of window 18.

The program sequence then reverts to step S4, causing the procedure for aligning the circuit board to be examined relative to the circuit board image to be repeated in accordance with steps S4 to S8. In step S9, the point or area to be examined is in turn displayed (FIG. 4g).

If the inquiry in step S10 reveals, on the other hand, that the list contains no further point to be examined, then the program sequence skips to step S12, in which the program is terminated.

Figure 4F:
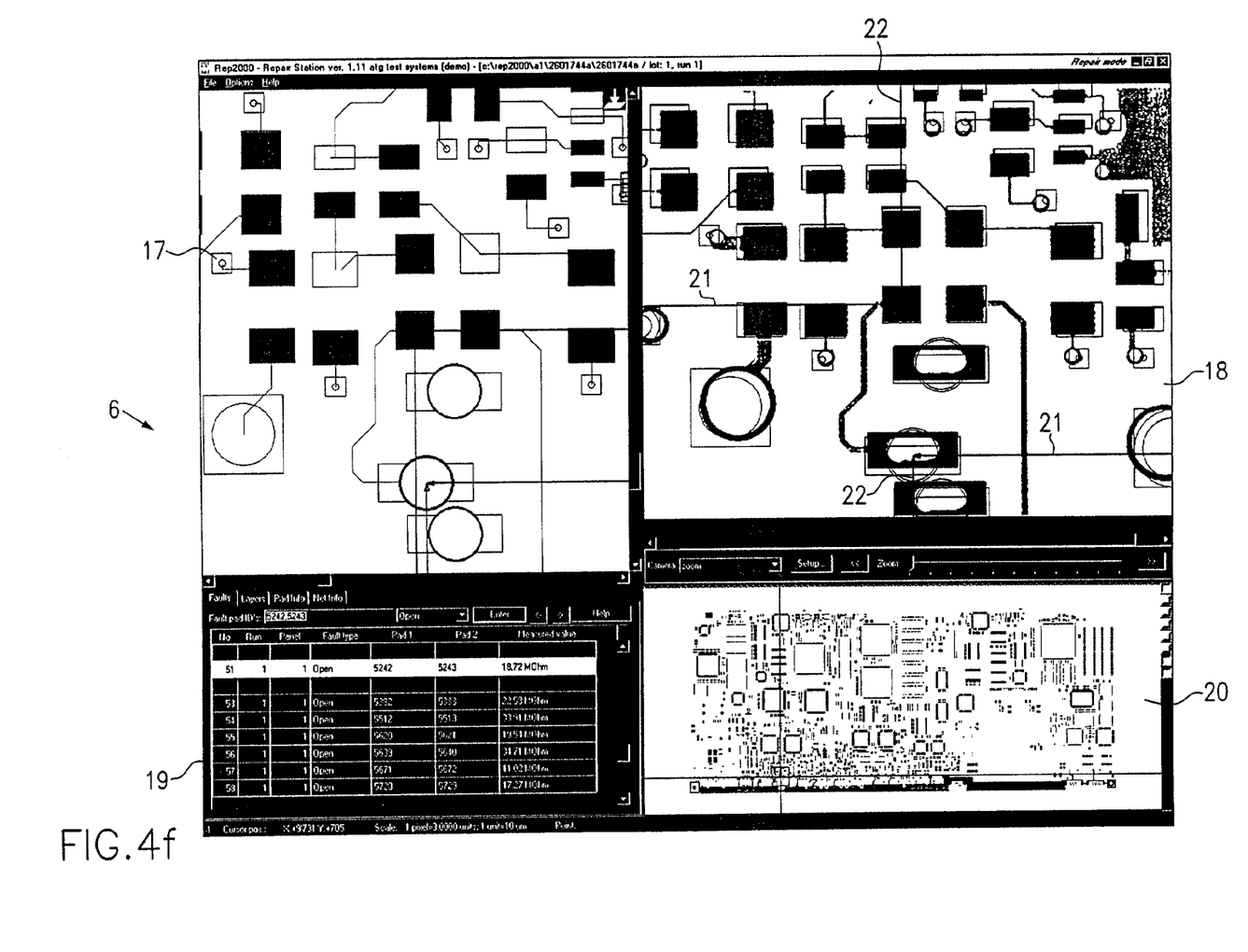

In the procedure described above, the CAD image 26 is displayed in window 17 in each case on the same scale and with the corresponding area to that of the circuit board image 24 in window 18. The CAD image 26 contains the data available to the circuit board tester 2 for testing the circuit board. In the example shown in FIGS. 4f and 4g, the CAD image 26 shows a circuit board test point in the form of a circle. The actual, correct form of the circuit board test point is however an elongated rectangle with an oval recess, as may be seen in window 18 with the aid of the camera image (FIGS. 4f and 4g). Such differences between the CAD data on which the measurements are based and the actual format arise during the processing of the original CAD data into CAD test data, in the course of which the format is modified. With the aid of the enlarged display as shown in FIGS. 4f and 4g, the user establishes that the electrical connection between the circuit board test points to be examined is in order, and that the measured defect is based on data which are not in agreement with the actual format. The connection is therefore judged to be correct, and the process sequence can move on to the next circuit board test point of the next defect contained in the list.

Figure 4G:
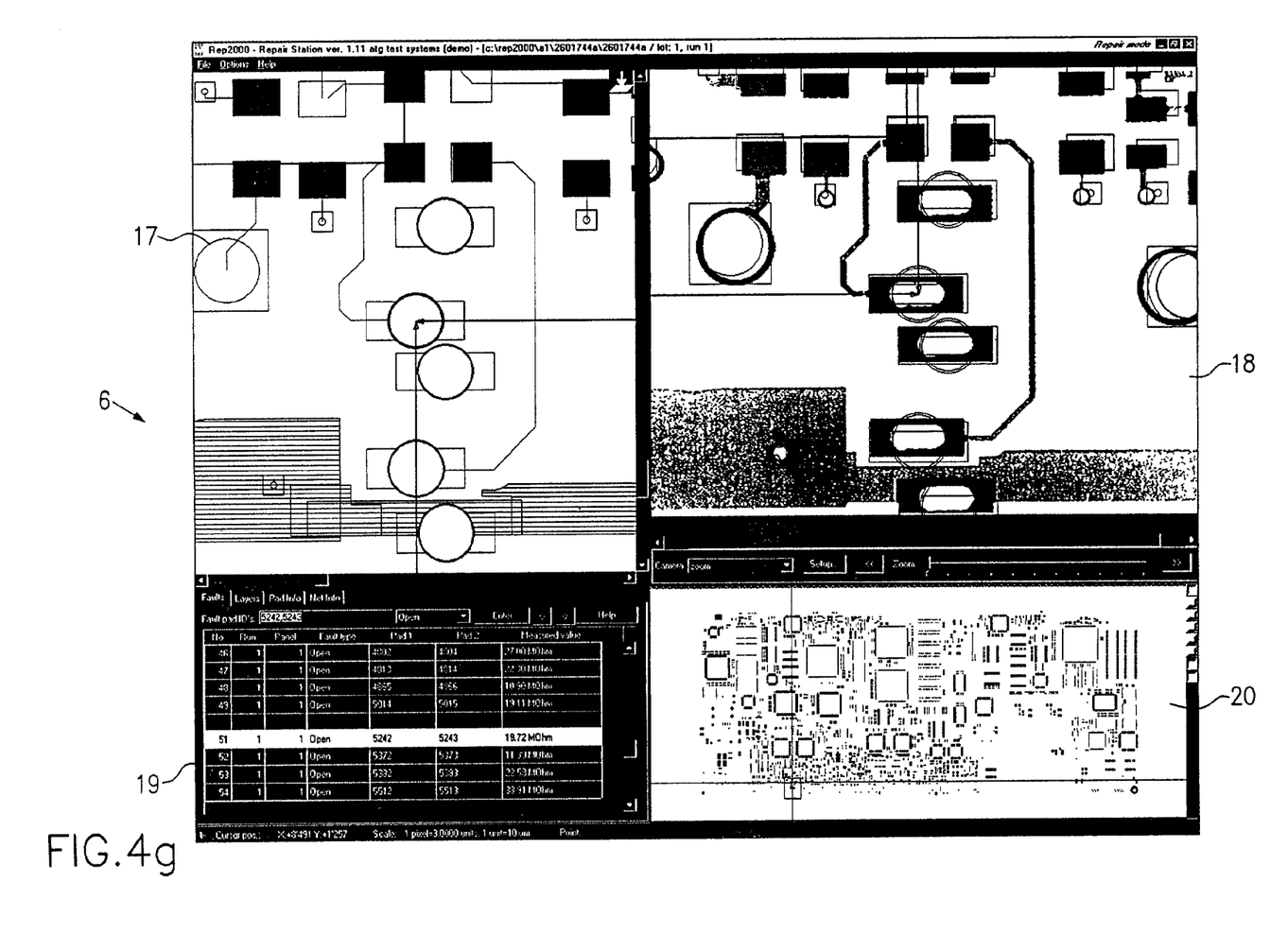

In the greatly enlarged view of the circuit board in FIGS. 4f and 4g, however, open- and short circuits may also be recognized visually. If such a defect is recognized, it is either rectified immediately or, if this is not possible, it is suitably marked. It may then be subject to subsequent reworking, if the fault can be rectified, otherwise the circuit board to be examined is scrap.

In the example described above, the two circuit board test points of the track to be examined are so close together that both are shown simultaneously in the maximum enlarged display (FIGS. 4f and 4g) in window 17 or 18. However, the tracks are often longer, so that it is not possible to show both end points of the tracks, the relevant circuit board test points, in windows 17 and 18 simultaneously. If the procedure described above is followed, then one circuit board test point will be displayed in one process run and the other circuit board test point in the other process run, while in the case of long tracks, the intermediate connecting section of the tracks can not be displayed in the maximum possible enlargement.

According to a preferred embodiment of the method according to the invention, in the case of such long tracks, the first circuit board test point associated with this track is examined and then, in the next program run involving steps S4 to S9, a section of the relevant track is shown instead of the other circuit board test point associated with this track. In each further program run, additional adjacent sections of the track to be examined are enlarged, until the whole track has been displayed, completely enlarged, in consecutive stages. At the end of the examination of a track the circuit board test point associated with this track, but not yet observed, is displayed in enlarged form. In this preferred variant of the method according to the invention, therefore, longer tracks that cannot be fully displayed in enlarged form in window 18 are shown in stages in consecutive adjacent sections. Preferably these sections overlap in part.

Figure 5:
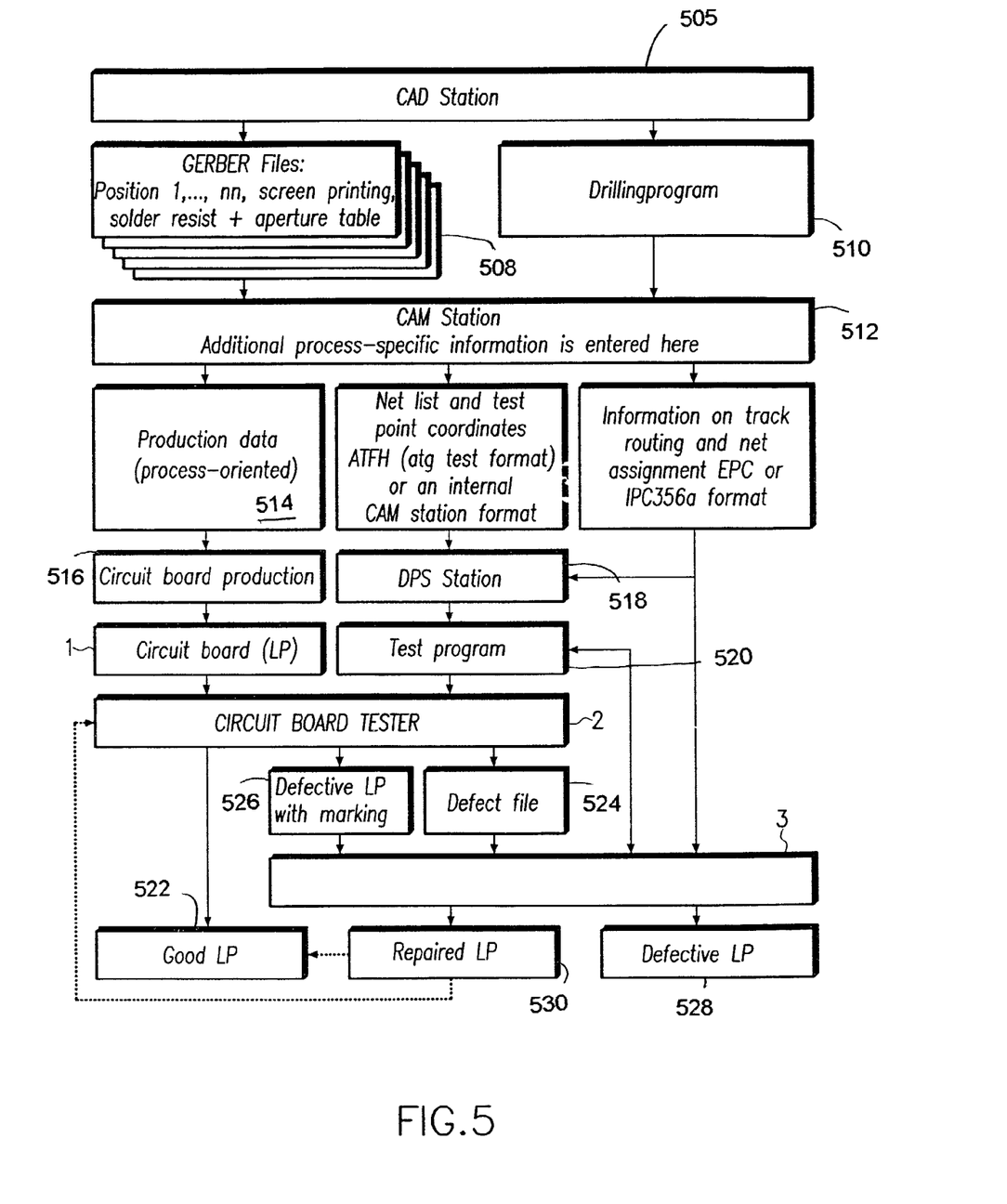
FIG. 5 is a block diagram showing the production sequence for the manufacture of circuit boards, from design of the circuit boards through to the final examination of the circuit boards in accordance with the inventive method.

FIG. 5 shows the manufacturing sequence for circuit boards. Firstly, a circuit board is designed at a CAD station 505. From the original CAD data, so-called GERBER files 508 are calculated. These contain screen printing and solder resist information, together with aperture tables, for each position. In parallel with this, a drilling program 510 is drawn up for the via holes to be made in the circuit board. The GERBER data and the drilling program are entered into a CAM station 512, accompanied by additional process-specific data. Production data for fabrication of the circuit boards, net lists and test point coordinates, and information on track routing and net assignment are derived from the CAM data. The net lists and test point coordinates are in ATFH format (Atg test format). The information on track routing and net assignments is in EP format or IPC 356A format.

The production data 514 are passed to the circuit board production unit 516, and the net lists and test point coordinates together with the information on track routing are sent to a DPS station 518. Circuit boards 1 are produced in the circuit board production unit and a test program 520 is generated in the DPS station 518. The test program 520 is played over on to the circuit board tester 2 so that the latter may be used to test the circuit boards 1, which are produced. If the test shows that the circuit board 1 is free from defects, it is assigned to a stack of good circuit boards 522. If on the other hand the test reveals that the circuit board has a defect, then it is marked as defective 526. A defect file 524 is created at the same time and is transmitted to the checking apparatus 3, so that the latter may be used to examine the defective circuit board in the manner described above. For this purpose the test program of the circuit board tester, which alone contains data on the circuit board test points, and the information on track routing and net assignment, are also transmitted to the checking apparatus, and are used to generate the CAD image 26 of window 17 and the circuit board images 24 of windows 18, 20.

The defective circuit boards 526 examined by the method according to the invention are either repaired 530 and then added to the stack 522 of good circuit boards or, if repair is impossible, they are sent for scrap 528.

The embodiment described above thus serves for the examination of individual circuit boards that have been tested by a circuit board tester. Within the framework of the invention, however, it is also possible to use the method to correct the test program. If, during the implementation of the method according to the invention, differences are found between the CAD image 26 and the actually correctly made tracks and circuit board test points as shown on camera image 25, then these differences may—in a development of the method according to the invention—be input via the keyboard 8 and stored. If all the differences relating to one circuit board type have been recorded, then the relevant data are transmitted by the checking apparatus 3 to the DPS station, where a revised program is generated. The method according to the invention may thus also be used for the correction of test programs based on production data.

The invention has been explained in detail above with the aid of an embodiment. The invention is not however restricted to this specific embodiment. Within the scope of the invention it is possible, for example, to use a high-resolution camera with a lens with fixed focal length instead of a camera with a zoom lens. The zooming or enlargement of the images displayed on the screen is then effected by calculation in the computer, by selecting suitable areas of the image recorded by the camera. Instead of a control pedal, any other kind of key may be used, although a control pedal is advantageous since it leaves the hands of the operator free to move the circuit board. In the embodiment described above, each of the predetermined areas is defined by individual circuit board test points. However it is also possible to define the areas independently of the test points, in particular as flat elements instead of points.

Important benefits of the method according to the invention are its very simple operation, quick location of the predetermined areas, and that only commercially available hardware, which can be assembled without costly mechanical or electrical structures, is required. The method according to the invention may thus be implemented very cost-effectively, and allows a high throughput of circuit boards to be examined.

The embodiment described above is intended for the examination of unloaded circuit boards. In principle, though, it is also possible to use this method for the examination of assembled circuit boards and in particular as an aid to the assembly of circuit boards. Instead of circuit board test points, relevant components may then be displayed on the screen or by means of a light pointer.

Within the scope of the invention it is also possible to provide voice control for the zoom operation, for example, so that the control pedal may be dispensed with.

The method according to the invention may also be modified so that the circuit board is aligned only once by movement, and the camera image is analyzed by means of a method of automatic image recognition, so that the individual elements (circuit board test points, tracks) recorded by the camera are determined. The camera image is then brought automatically into congruence with the circuit board image, since the circuit board test points of the camera image and of the circuit board image, which are to be brought into line with one another are assignable to one another.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of examining a circuit board in a predetermined area of the circuit board using an apparatus that has a stationary camera and a display unit, the method comprising the following steps:
    a) positioning a circuit board to be examined in a scanning zone of the camera, wherein a camera image and a circuit board image separate from the camera image are shown on the display unit on the same scale, wherein the circuit board image is generated by a computer aided design (CAD) system;
    b) moving of the circuit board to be examined to improve congruence between the camera image and the circuit board image;
    c) enlarging the camera image and the circuit board image on the display unit in the same ratio;
    d) bringing the camera image to coincide more closely with the circuit board image, and
    e) displaying the predetermined area so that an enlarged view of the predetermined area of the circuit board to be examined is visible on the display unit.

2. A method according to claim 1, wherein the step of bringing the camera image to coincide more closely with the circuit board image comprises moving the circuit board.

3. A method according to claim 2, further comprising displaying the circuit board image in a predetermined section of the display unit with the predetermined area to be examined being approximately in the center of the predetermined section of the display unit.

4. A method according to claim 3, wherein the predetermined area to be examined corresponds to a defect in the circuit board which has been detected by a circuit board tester.

5. A method according to claim 4, wherein each predetermined area to be examined is defined in the circuit board image by a circuit board test point linked to a track on the circuit board which has been judged to be defective by the measurements made in advance on the circuit board tester, and indicated by arrows, the tips of which end at the circuit board test point.

6. A method according to claim 4, wherein each area to be examined corresponds to a section of a track, judged as defective and shown on the display unit, wherein several adjacent sections of the track are shown consecutively on the display unit in an enlarged view.

7. A method according to claim 6, further comprising generating a defect file containing a list of measured defects, and actuating a single key to initiate steps a) and c), so that all areas to be examined may be shown on the display unit in an enlarged view solely by moving the circuit board and actuating the key.

8. A method according to claim 7, wherein a control pedal is used as key.

9. A method according to claim 7, further comprising repeating the step of enlarging the camera image and the circuit board image on the display unit in the same ratio two or three times for each area to be examined, wherein the enlargement factor for each enlargement of the camera image and the circuit board image does not exceed 20.

10. A method according to claim 9, wherein the display unit has two sections, wherein the circuit board image and the camera image are displayed in one section, and the other section displays an image of the circuit board on the same scale as the circuit board image and the camera image, and showing both circuit board test points and tracks.

11. A method according to claim 1, wherein the step of bringing the camera image to coincide more closely with the circuit board image is effected by an automatic image recognition method, which analyses the camera image and brings it automatically into congruence with the circuit board image.

12. A method according to claim 11, further comprising displaying the circuit board image in a predetermined section of the display unit with the predetermined area to be examined being approximately in the center of the predetermined section of the display unit.

13. A method according to claim 12, wherein the predetermined area to be examined corresponds to a defect in the circuit board which has been detected by a circuit board tester.

14. A method according to claim 13, wherein each predetermined area to be examined is defined in the circuit board image by a circuit board test point linked to a track on the circuit board which has been judged to be defective by the measurements made in advance on the circuit board tester, and indicated by arrows, the tips of which end at the circuit board test point.

15. A method according to claim 13, wherein each area to be examined corresponds to a section of a track, judged as defective and shown on the display unit, wherein several adjacent sections of the track are shown consecutively on the display unit in an enlarged view.

16. A method according to claim 15, further comprising generating a defect file containing a list of measured defects, and actuating a single key to initiate steps a) and c), so that all areas to be examined may be shown on the display unit in an enlarged view solely by moving the circuit board and actuating the key.

17. A method according to claim 16, wherein a control pedal is used as key.

18. A method according to claim 17, further comprising repeating the step of enlarging the camera image and the circuit board image on the display unit in the same ratio two or three times for each area to be examined, wherein the enlargement factor for each enlargement of the camera image and the circuit board image does not exceed 20.

19. A method according to claim 18, wherein the display unit has two sections, wherein the circuit board image and the camera image are displayed in one section, and the other section displays an image of the circuit board on the same scale as the circuit board image and the camera image, and showing both circuit board test points and tracks.

20. A method according to claim 1, further comprising displaying the circuit board image in a predetermined section of the display unit with the predetermined area to be examined being approximately in the center of the predetermined section of the display unit.

21. A method according to claim 1, wherein the predetermined area to be examined corresponds to a defect in the circuit board which has been detected by a circuit board tester.

22. A method according to claim 21, wherein each predetermined area to be examined is defined in the circuit board image by a circuit board test point linked to a track on the circuit board which has been judged to be defective by the measurements made in advance on the circuit board tester, and indicated by arrows, the tips of which end at the circuit board test point.

23. A method according to claim 21, wherein each area to be examined corresponds to a section of a track, judged as defective and shown on the display unit, wherein several adjacent sections of the track are shown consecutively on the display unit in an enlarged view.

24. A method according to claim 21, further comprising generating a defect file containing a list of measured defects, and actuating a single key to initiate steps a) and c), so that all areas to be examined may be shown on the display unit in an enlarged view solely by moving the circuit board and actuating the key.

25. A method according to claim 24, wherein a control pedal is used as key.

26. A method according to claim 1, further comprising repeating the step of enlarging the camera image and the circuit board image on the display unit in the same ratio two or three times for each area to be examined, wherein the enlargement factor for each enlargement of the camera image and the circuit board image does not exceed 20.

27. A method according to claim 1, wherein the display unit has two sections, wherein the circuit board image and the camera image are displayed in one section, and the other section displays an image of the circuit board on the same scale as the circuit board image and the camera image, and showing both circuit board test points and tracks.

28. An apparatus for examining a circuit board in a predetermined area of the circuit board, the apparatus comprising:
   a stationary camera for generating a camera image of the circuit board;
   a display unit linked to the camera for displaying the camera image;
   a device to enlarge the camera image and a circuit board image on the display unit in the same ratio, wherein the circuit board image is generated by a computer aided design (CAD) system;
   means for positioning of a circuit board to be examined in the scanning zone of the camera, wherein the camera image and the circuit board image separate from the camera image are shown on the display unit on the same scale;
   means for moving the circuit board to be examined, to make the camera image as congruent as possible with the circuit board image;
   means for bringing the camera image to coincide more closely with the circuit board image after enlargement, and
   means for display of the predetermined area to be examined, so that an enlarged view of the predetermined area of the circuit board to be examined is visible on the display unit.

29. An apparatus according to claim 28, further comprising a computer with a central processor unit, a data and program memory and a video screen functioning as the display unit.

30. An apparatus according to claim 28, further comprising a circuit board tester for generating a defect file.

31. An apparatus according to claim 28, wherein the camera has a zoom lens, with a focal length which is electrically controlled.

32. An apparatus according to claim 28, wherein the camera has a focussing device.

33. A method of display in an apparatus for examining a circuit board in a predetermined area of the circuit board, the display method comprising:
   generating a CAD image window showing circuit board test points;
   generating a circuit board image window showing the predetermined area of an exemplary circuit board and for showing an image of the predetermined area of a circuit board to be examined, the predetermined area of the exemplary circuit board being used to align the image of the predetermined area of the circuit board to be examined; and
   generating a defects list window showing potential defects with the circuit board to be examined, which was generated by a circuit board tester.

34. A display method according to claim 33, further comprising generating a whole circuit board window showing the location of the predetermined area on the circuit board.

35. A display method according to claim 33, further comprising generating indicia extending between the circuit board test points in the CAD image window and the image of the predetermined area of the circuit board to be examined when aligned to the predetermined area of the exemplary circuit board.

36. A display method according to claim 33, wherein CAD image window displays an image generated by computer aided design (CAD) system that corresponds to the image of the predetermined area in the circuit board image window.

* * * * *